United States Patent [19]
Leroy et al.

[11] Patent Number: 6,113,641
[45] Date of Patent: Sep. 5, 2000

[54] PROSTHESIS FOR THE OBTURATION OF A HERNIAL CANAL

[75] Inventors: Joel Leroy, Bully les Mines; Axel Arnaud, Neuilly sur Seine, both of France

[73] Assignee: Ethicon, Inc., Somerville, N.J.

[21] Appl. No.: 09/138,732

[22] Filed: Aug. 24, 1998

[51] Int. Cl.$^7$ ............................. A61F 2/02; A61B 17/08
[52] U.S. Cl. ................. 623/23.075; 606/151; 606/213; 600/37
[58] Field of Search ..................... 623/11; 606/151, 606/213; 600/37

[56] References Cited

U.S. PATENT DOCUMENTS

| | | |
|---|---|---|
| 636,952 | 11/1899 | Chaney . |
| 2,683,136 | 7/1954 | Higgins .................. 260/78.3 |
| 2,761,444 | 9/1956 | Luck ........................ 128/92 |
| 3,054,406 | 9/1962 | Usher ..................... 128/334 |
| 3,124,136 | 3/1964 | Usher ..................... 128/334 |
| 3,707,150 | 12/1972 | Montgomery et al. ......... 128/334 R |
| 3,874,388 | 4/1975 | King et al. ............. 128/334 R |
| 4,007,743 | 2/1977 | Blake .................. 128/334 R |
| 4,013,569 | 3/1977 | Chiu et al. ............ 252/8.55 D |
| 4,347,847 | 9/1982 | Usher ..................... 128/334 |
| 4,548,202 | 10/1985 | Duncan .................... 128/334 |

(List continued on next page.)

FOREIGN PATENT DOCUMENTS

| | | |
|---|---|---|
| 0 544 485 B1 | 11/1992 | European Pat. Off. . |
| 0 544 485 A1 | 6/1993 | European Pat. Off. . |
| 0 614 650 A2 | 2/1994 | European Pat. Off. . |
| 0 677 297 A1 | 10/1995 | European Pat. Off. . |
| 0 692 225 A2 | 1/1996 | European Pat. Off. . |
| 0 698 395 A1 | 2/1996 | European Pat. Off. . |
| 0 719 527 A1 | 7/1996 | European Pat. Off. . |
| 0 744 162 A2 | 11/1996 | European Pat. Off. . |
| 0 537 955 B1 | 12/1996 | European Pat. Off. . |
| 0 797 962 A2 | 10/1997 | European Pat. Off. . |
| WO 94/27535 | 12/1984 | WIPO . |
| WO 90/14796 | 12/1990 | WIPO . |
| WO 92/06639 | 4/1992 | WIPO . |
| WO 92/13500 | 8/1992 | WIPO . |
| WO 92/19162 | 11/1992 | WIPO . |
| WO 93/03685 | 3/1993 | WIPO . |
| WO 93/17635 | 9/1993 | WIPO . |
| WO 94/17747 | 8/1994 | WIPO . |
| WO 95/07666 | 3/1995 | WIPO . |
| WO 95/13762 | 5/1995 | WIPO . |
| WO 95/31140 | 11/1995 | WIPO . |
| WO 95/32687 | 12/1995 | WIPO . |
| WO 96/03091 A1 | 2/1996 | WIPO . |
| WO 96/03165 A1 | 2/1996 | WIPO . |
| WO 96/09795 | 4/1996 | WIPO . |
| WO 96/14805 | 5/1996 | WIPO . |
| WO 96/41588 | 12/1996 | WIPO . |
| WO 97/02789 | 1/1997 | WIPO . |
| WO 97/22310 | 6/1997 | WIPO . |

OTHER PUBLICATIONS

Research Development Journal—Feb. 1998—Issue #406—"Preparation of Absorbable Surgical Mesh" (40624)p. 130; "Preparation of a Coating Copolymer for use in Absorbable Suture Material or Surgical Mesh" (40634) p. 147: Preparation of Absorbable Polymer for use in Suture Material or Surgical Mesh (40639) p. 158—Issue #408—"Processing of Polypropylene Surgical Mesh" (40830) p. 345.

*Primary Examiner*—Paul B. Prebilic

[57] ABSTRACT

A prosthesis to obturate a hernial canal includes a first part made of surgical material and configured in such a way as to deform under the effect of intra-abdominal pressure, to oppose such pressure elastically and to spread the force at the hernial canal over a portion of the inside face of the wall of a hernial cavity; and a second part for positioning in contact with the inside face of the wall of the hernial cavity and positioned annularly about the first part, whereby force exerted at the hernial canal is spread over a portion of the inside wall of the hernial cavity via the second part.

10 Claims, 2 Drawing Sheets

U.S. PATENT DOCUMENTS

| | | | |
|---|---|---|---|
| 4,633,873 | 1/1987 | Dumican et al. | 128/334 |
| 4,769,038 | 9/1988 | Bendavid et al. | 623/13 |
| 4,854,316 | 8/1989 | Davis | 128/334 R |
| 4,917,089 | 4/1990 | Sideris | 606/215 |
| 5,002,551 | 3/1991 | Linsky et al. | 606/151 |
| 5,021,059 | 6/1991 | Kensey et al. | 606/213 |
| 5,092,884 | 3/1992 | Devereux et al. | 623/11 |
| 5,108,420 | 4/1992 | Marks | 606/213 |
| 5,108,421 | 4/1992 | Fowler | 606/213 |
| 5,116,357 | 5/1992 | Eberbach | 606/213 |
| 5,122,155 | 6/1992 | Eberbach | 606/213 |
| 5,141,515 | 8/1992 | Eberbach | 606/151 |
| 5,147,374 | 9/1992 | Fernandez | 606/151 |
| 5,171,148 | 12/1992 | Wasserman et al. | 433/215 |
| 5,219,077 | 6/1993 | Transue . | |
| 5,246,455 | 9/1993 | Shikani | 623/10 |
| 5,249,682 | 10/1993 | Transue | 206/438 |
| 5,254,133 | 10/1993 | Seid | 606/215 |
| 5,258,000 | 11/1993 | Gianturco . | |
| 5,292,328 | 3/1994 | Hain et al. | 606/151 |
| 5,297,714 | 3/1994 | Kramer | 227/175 |
| 5,316,543 | 5/1994 | Eberbach | 600/37 |
| 5,334,217 | 8/1994 | Das . | |
| 5,356,432 | 10/1994 | Rutkow et al. | 623/11 |
| 5,366,460 | 11/1994 | Eberbach | 606/151 |
| 5,370,650 | 12/1994 | Tovey et al. . | |
| 5,397,331 | 3/1995 | Himpens et al. | 606/151 |
| 5,397,332 | 3/1995 | Kammerer et al. | 606/151 |
| 5,456,720 | 10/1995 | Schultz et al. | 623/12 |
| 5,569,273 | 10/1996 | Titone et al. | 606/151 |
| 5,578,045 | 11/1996 | Das | 606/151 |
| 5,686,090 | 11/1997 | Schilder et al. | 424/423 |
| 5,725,552 | 3/1998 | Kotula et al. | 606/213 |
| 5,944,738 | 8/1999 | Amplatz et al. | 606/213 |
| 5,964,781 | 10/1999 | Mollenauer et al. | 606/213 |
| 5,976,174 | 11/1999 | Ruiz | 606/151 |

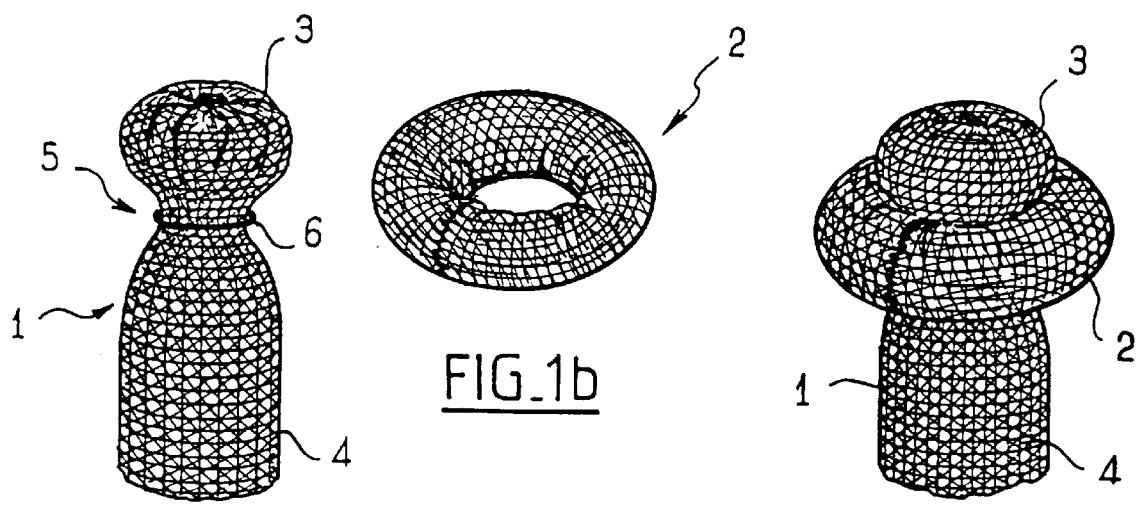
FIG_1a   FIG_1b
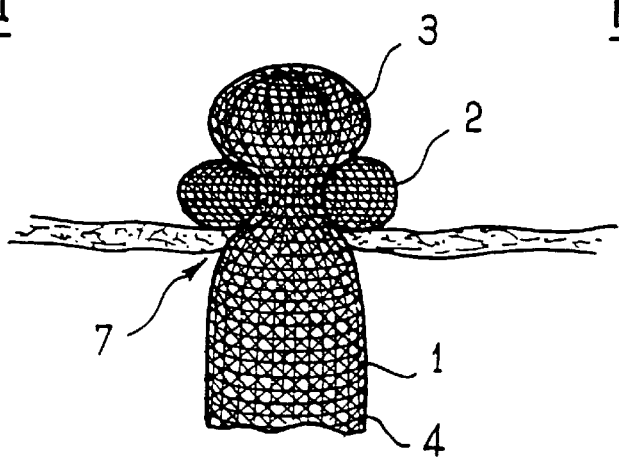
FIG_2
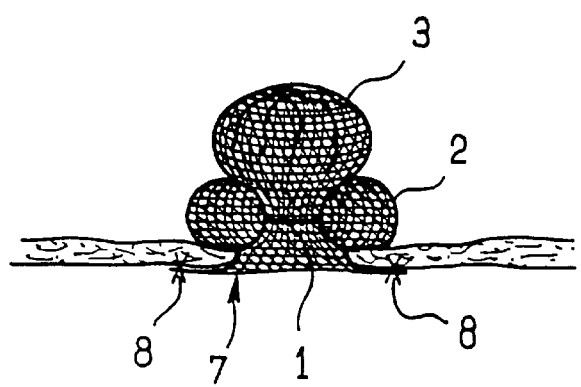
FIG_3a
FIG_3b

PROSTHESIS FOR THE OBTURATION OF A HERNIAL CANAL

FIELD OF THE INVENTION

The present invention relates to prostheses used to obturate a hernial canal.

BACKGROUND OF THE INVENTION

In conventional techniques, hernial canal repair is generally carried out by suturing. However, that method of repair is not entirely satisfactory: given that the suture line is subject to a large amount of tension, there is a risk of tearing, which could then lead to recurrence of the hernia.

In order to mitigate that disadvantage, tension-free hernia repair techniques have been proposed.

In particular, a known technique is to position a sheet of synthetic prosthesis material, of tulle mesh or analogous type, on the hernial canal, to reinforce or replace the weakened tissue. For example, in open surgical repair of an inguinal hernia, a band may be used which is positioned on the inguinal ring, on the side remote from the peritoneum, this band being slit to allow the spermatic cord to pass, and the two tails of the band are then wound around the spermatic cord. The barrier thus created makes it possible for the inguinal canal floor to regenerate.

Such a barrier-forming patch may also be positioned by non-invasive surgery. A device using a trocar to deploy prosthesis sheets inside the abdominal cavity, on the peritoneum, is described in EP 0 544 485, for example.

Another tension-free repair technique, which may be used in combination with the above-mentioned technique consists in obturating the hernial canal with a prosthesis obturation device.

Usually a surgeon makes an obturating device by rolling a patch cut out from prosthesis material in order to obtain a cylinder of appropriate dimensions.

Other shapes of prosthesis obturating device are also used, such as rectangular obturators, conical obturators or necked obturators enabling them to be positioned relative to the hernial canal. The following may be consulted in that respect.

'Prostheses in Abdominal Wall Hernia', Robert Bendavid, RG Landes Company, Austin, pages 375–379, 380–382, 383–388, 389–398, 408–410, 411–412, 413–414, 446–449, and also U.S. Pat. No. 5,116,357 and U.S. Pat. No. 5,356,432.

Other known prostheses are constituted by cylindrical obturators terminating at one end with prosthesis sheets for suturing by the surgeon to the non-weakened muscles on either side of the hernial canal to complement the obturation provided by the obturator. In that respect reference may advantageously be made to U.S. Pat. No. 5,219,077, U.S. Pat. No. 5,249,682 or U.S. Pat. No. 5,147,374.

The object of the invention is to propose a prosthesis obturating device which is simple in structure and simple to manipulate and which is also very effective.

SUMMARY OF THE INVENTION

The invention therefore provides a prosthesis obturating device to obturate the hernial canal, the obturating device comprising a part made of surgical material which is brought to bear on the inside face of the wall of the hernial cavity, and being characterized in that said part is configured in such a way as to deform under the effect of intra-abdominal pressure and to oppose said pressure elastically and to spread the force at the hernial canal over a portion of the inside face of the wall of the hernial cavity.

BRIEF DESCRIPTION OF THE DRAWINGS

Other characteristics and advantages of the invention can be seen from the following description. This description is intended as an illustration and is not limiting. It should be read in consultation with the accompanying drawings where:

FIGS. 1a and 1b are perspective diagrams of the two parts of the prosthesis in one possible embodiment of the invention;

FIG. 2 is a perspective diagram of the prosthesis constituted by the two parts shown in FIGS. 1a and 1b;

FIGS. 3a and 3b illustrate the two stages of the positioning of the prosthesis on the hernial canal.

DETAILED DESCRIPTION OF THE INVENTION

Figure 4A:
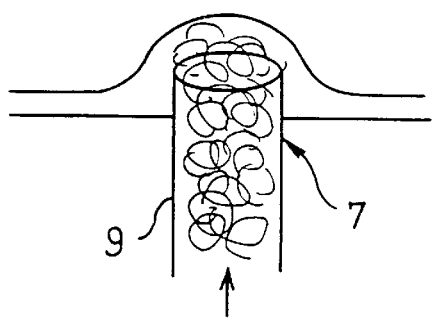
FIGS. 4a to 4d illustrate the positioning of the prosthesis in another possible embodiment of the invention.

The prosthesis obturating device illustrated in FIGS. 1a, 1b and 2 comprises two parts: a part referenced 1 constitutes the body of the obturating device, the other part, referenced 2, is of toroidal shape and is positioned over part 1 to surround it annularly.

The body-forming part 1 is constituted by a pouch made of a sheet of synthetic or natural material configured with a swollen head 3 and a base 4 of substantially cylindrical form, which is open at its end opposite from the swollen head 3.

The head 3 and the base 4 are joined by a narrow neck 5 defined by a tightening cord 6 which surrounds said part 1 between the head 3 and the base 4 to forbid the invagination of the head in case of a vertical pressure.

The part 2 of toroidal shape is also made of a sheet of synthetic or natural material. It has an inside annular diameter substantially equal to the outside diameter of the neck 5. As is shown in FIG. 2, it is to be positioned on part 1 at the level of said neck 5 which is of a height such that, once the part 2 is positioned on the neck 5 it is substantially held in place by being clamped between the head 3 and the base 4.

The material(s) from which these parts are made is selected so as to be inert and infection-resistant, and to be biocompatable with tissue.

Numerous biocompatible absorbable and nonabsorbable materials can be used for parts 1 and 2. Suitable nonabsorbable materials for use in parts 1 and 2 include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophtalamide (nylon 61) copolymers and blends thereof), polyesters (e.g polyethylene terephtalate, polybutyl terphtalate, copolymers and blends thereof), fluoropolymers (e.g expanded or not polytetrafluoroethylene) and polyolefins (e.g polypropylene including isotactic and syndiotactic polypropylene and blends thereof, as well as, blends composed predominately of isotactic or syndiotactic polypropylene blended with heterotactic polypropylene and polyethylene).

Suitable absorbable materials for use in parts 1 and 2 include, but are not limited to, homopolymers and copolymers of glycolide, lactide (which includes L-, D-, and mesoforms of lactide and mixtures thereof), ε-caprolactone, p-dioxanone, trimethylene, carbonate, 1,4-dioxepan-2-one, poly(alkylene axalate), and mixtures of such polymers with each other and with other compatible absorbable compositions as those described; for example, in U.S. Pat. No. 636,952 and U.S. Pat. No. 2,683,136.

The sheets that comprise parts 1 and 2 may be constructed in a variety of ways and may be films, felts, knits, wovens, crochets, braided materials or combinations thereof. Numerous surgical meshes, nets or films have been described in the literature and reference may be made to U.S. Pat. No. 2,761,444; U.S. Pat. No. 3,054,406; U.S. Pat. No. 3,124,136; U.S. Pat. No. 4,347,847; U.S. Pat. No. 4,633,873; U.S. Pat. No. 4,769,038; U.S. Pat. No. 5,092,884; U.S. Pat. No. 5,292,328; U.S. Pat. No. 5,569,273; PCT/GB95/01786 and EP 0 698 395 A1.

As an example of sizing, in the case of a hernial canal of a diameter of 4 cm, the base 4 may be of the order of 5 cm high, the height of the head 3 of the order of 2 cm, and total height of the obturating device of the order of 9 cm; the diameter of the cylindrical base 4 and that of the head 5 are of the order of 3 cm, whereas the toroidal part 2 has an outside annular diameter of 5 cm and an inside annular diameter of 2.5 cm.

Such a prosthesis obturating device is inserted in open surgery.

The toroidal part 2 is inserted into the body 1.

Once the toroidal part 2 is positioned on the body 1 and after dissecting the peritoneal sac and pushing it back into the cavity of the hernia, the surgeon positions the head 3 of the obturating device in front of the hernial canal, referenced 7 in FIGS. 3a and 3b.

Then the surgeon inserts the obturating device in said hernial canal 7 in order to position the head 3 and the toroidal part 2 on the inside face of the hernia, the base 4 extending from the superficial orifice of the hernial canal 7 to the outside of the cavity of the hernia.

After inserting the head 3 and the toroidal part 2 into the hernial cavity, the surgeon pulls the base 4 gently outwards in such a way as to bring the toroidal part 2 in contact with the inside face of the wall of the hernial cavity. (FIG. 3a).

The surgeon then cuts out a plurality of tails 8 in the base 4, which tails are folded over the outside face of the wall of the hernial cavity, and then said tails 8 are sutured to said wall (FIG. 3b).

This description shows that the structure is extremely easy to insert.

The structure is also very effective.

In particular, the swollen head 3 of the prosthesis elastically opposes the internal pressure exerted in the hernial cavity at the canal 7 of the hernia. It deforms by flattening onto the toroidal part 2, in such a way that the force exerted at the hernial canal 7 is spread, via the toroidal part 2, over a large portion of the wall of the hernial cavity, around the inside orifice of the canal 7.

Of course, other variant embodiments are possible.

In particular, the part of the prosthesis to be inserted inside the hernia may be of a shape different from that of the prosthesis obturating device described above.

In addition, materials other than materials in sheet form may be considered. For example the prosthesis may be constituted by a ball of fiber or foam to be injected inside the hernial cavity to absorb abdominal pressure elastically by bearing down around the hernial canal, in order to spread the force at the hernial canal over the edges of the wall of the hernial cavity which surrounds said canal.

Figure 4B:
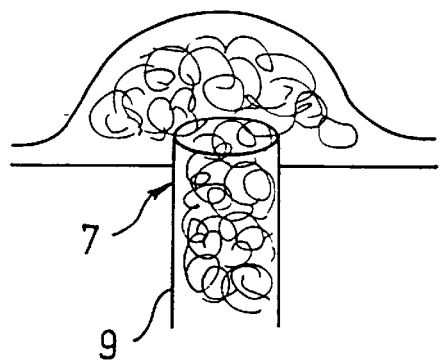
Figure 4C:
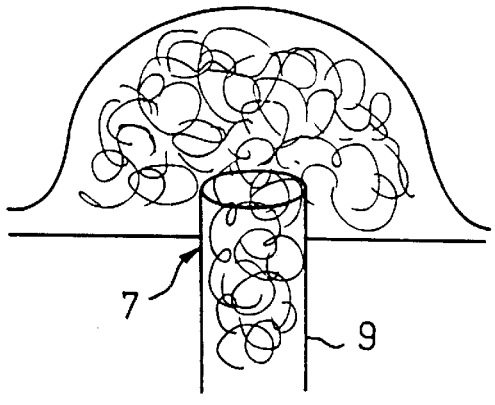
Figure 4D:
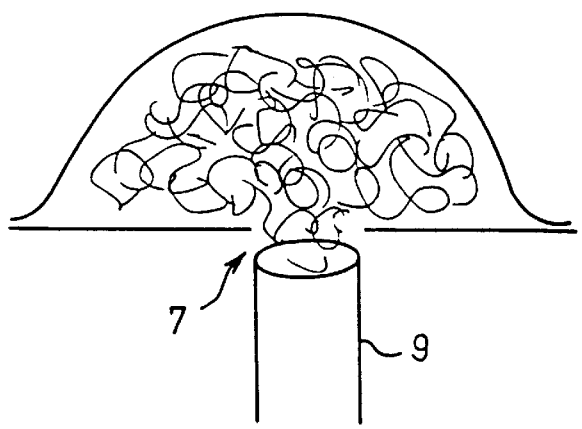

A fiber-ball or foam prosthesis may be made of injected prolene type, as illustrated in FIGS. 4a–4d, being injected through the hernial canal 7 in the space between the wall of the hernial cavity and the peritoneum.

An applicator tube 9 is used for this purpose, positioned by the surgeon in hernial canal 7. The surgeon presses the piston to inject the foam or fiber contained in the applicator 9. Then once the applicator has been emptied, the surgeon removes the applicator, thereby spreading part of the injected prosthetic material so that it fills the hernial canal 7.

What is claimed is:

1. A prosthesis to obturate a hernial canal, the prosthesis comprising, a first part comprising the body of the prosthesis and made of surgical material and being characterized in that said first part is configured in such a way as to deform under the effect of intra-abdominal pressure, to oppose said pressure elastically and to spread the force at the hernial canal over a portion of the inside face of the wall of a hernial cavity; and a second part for positioning in contact with the inside face of the wall of the hernial cavity, said second part being positioned annularly about said first part, whereby force exerted at the hernial canal is spread over a portion of the inside wall of the hernial cavity via said second part.

2. A prosthesis according to claim 1, wherein the first part is configured in such a way as to extend through the hernial canal and to be folded down over the outside face of the wall of the hernial cavity for fixing of the first part on the borders of the aperture.

3. A prosthesis according to claim 1, wherein the prosthesis is constructed from one or more sheet materials.

4. A prosthesis according to claim 3, wherein the first part comprises a swollen head extended by a base to which it is joined, a third part which surrounds the first part at the point where the head and the base are joined, thereby forming a narrow neck at said point, and wherein the second part is toroidal in configuration and surrounds the first part at the narrow neck, and wherein the toroidal second part and the swollen head together bear against the inside face of the wall of the hernial cavity, thereby spreading the force exerted at the hernial canal over a portion of the inside wall of the hernial cavity.

5. A prosthesis according to claim 1, wherein the prosthesis is constructed of a fiber or a foam material.

6. A prosthesis according to claim 1, wherein at least one of the first and second parts is made from a non-absorbable material.

7. A prosthesis according to claim 6, wherein said first or second part is made from a material selected from the group consisting of cotton, linen, silk, polyamides, polyesters, fluoropolymers, and polyolefins.

8. A prosthesis according to claim 7 wherein said first or second part is made from a material selected from the group comprising polyhexamethylene adipamide, polyhexamethylene sebacamide, polycapramide, polydodecanamide, polyhexamethyleneisophtalamide, polyethylene terephthalate, polybutyl terphtalate, polytetrafluoroethylene, polypropylene and polyethylene.

9. A prosthesis according to claim 1, wherein at least one of the first and the second parts is made from an absorbable material.

10. A prosthesis according to claim 9, wherein said first or second part is made from a material selected from the group consisting of homopolymers and copolymers of glycolide, lactide, ε-caprolactone, p-dioxanone, trimethylene carbonate, 1,4-dioxepan-2-one, and poly(alkyleneoxalate).

* * * * *